United States Patent [19]

Peterson

[11] Patent Number: 4,472,394

[45] Date of Patent: Sep. 18, 1984

[54] METHOD FOR INCREASING WEIGHT IN DOMESTIC ANIMALS

[75] Inventor: Arnold Peterson, Flanders, N.J.

[73] Assignee: G. D. Searle & Co., Skokie, Ill.

[21] Appl. No.: 533,700

[22] Filed: Sep. 19, 1983

[51] Int. Cl.³ ............................................. A61K 31/56
[52] U.S. Cl. .................................................... 424/243
[58] Field of Search ......................................... 424/243

[56] References Cited

U.S. PATENT DOCUMENTS 3,941,880 2/1976 Short .................................... 424/243

Primary Examiner—Elbert L. Roberts
Attorney, Agent, or Firm—John J. McDonnell

[57] ABSTRACT

The present invention relates to a method for promoting weight gain in a domestic farm animal which comprises subcutaneously implanting a slow-release implant which contains norgestomet in a quantity such that at least 75 mcg/day to a maximum of 200 mcg/day is administered for a period of from 60 to 210 days.

4 Claims, No Drawings

METHOD FOR INCREASING WEIGHT IN DOMESTIC ANIMALS

BACKGROUND OF THE INVENTION (a) Field of the Invention

The present invention relates to a method for promoting weight gain in domestic farm animals which comprises subcutaneously implanting a slow-release implant which contains norgestomet in a quantity such that from about 75 to 200 mcg/day is administered for a period of from about 60 to 210 days. In a particular aspect of the invention the slow-release implant is a silastic type implant.

It has long been important to attempt to increase the weight of domestic farm animals eventually sold for consumption. A great deal has been done with chickens, lambs, heifers, etc. and the use of steroids, see e.g., Sci. Agron. Rennes, pg. 74–87 (1981). A number of different anabolic steroids are already commercially useful in producing this effect.

Norgestomet, a progestin, has the structure:

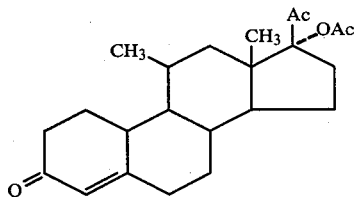

It is useful in controlling estrus and initiating the onset of puberty in female domestic farm animals when administered through a silastic implant for a period of from about 6 to about 21 days in doses of about 100–200 mcg/day.

(b) Information Disclosure

U.S. Pat. Nos. 3,992,518 and 3,946,106 describe microsealed delivery devices (silastic) and methods for making the same which are useful in the practice of this invention. U.S. Pat. No. 3,527,778 describes certain 11-lower alkyl steroids, in particular 17$\zeta$-acetoxy-11$\beta$-methyl-19-nerpregn-4-ene-3,20 dione or norgestomet. U.S. Pat. No. 3,941,880 describes the use of norgestomet for controlling estrus in female bovines. U.S. Pat. No. 3,860,701 describes a hydron drug delivery system useful in the practice of the invention. U.S. Pat. No. 3,892,855 describes another method of using norgestomet in controlling estrus in female bovines.

SUMMARY OF THE INVENTION

It has been surprisingly discovered that when norgestomet is administered in doses of about 75 mcg to 200 mcg per day via a subcutaneous implant for periods of from about 60 to 210 days, domestic farm animals show appreciable weight gains. In addition, it has been discovered that steroid compounds can be released at uniform rates for extended time periods, i.e. 60 or more days, from silastic type implants.

A preferred embodiment of the invention is where the implant is a silastic type implant and where the dose is about 100–150 mcg/day for a period of about 130–190 days. The invention may be practiced using any suitable subcutaneous implant device known in the art and used on domestic farm animals, e.g., heifers, lambs, pigs, which would benefit from increased weight gain. The implant may be located at any convenient standard release point, e.g., the ear. The implant must be such that a continuous release of medicament of at least 75 mcg/day is achieved up to a maximum of 200 mcg for a period of at least 60 days up to 210 days. The exact time period may vary from animal to animal but in general if at least 75 mcg/day over 60 days is used, a significant increase in weight is achieved.

The invention will appear more fully from the examples which follow. These examples are given by way of illustration only and are not to be construed as limiting the invention either in spirit or in scope, as many modifications by one skilled in the art are possible. While the examples are from heifers only, it is easy to see how this invention could be applied to any animal where weight gain is important.

DESCRIPTION OF THE PREFERRED EMBODIMENTS

Four studies were designed to measure differences in individual performance by body weight gain resulting from long-term release of the progestin, norgestomet. Four trials involving 324 treated heifers and 273 non-treated (controls) heifers were conducted. Comparisons to estrus control were made to test for correlation.

EXAMPLE 1

Forty Hereford X Simmental heifer calves, approximately 4–5 months of age were given a subcutaneous silastic ear implant 1.4 cm long X 0.38 cm diameter containing 27.00 mg of norgestomet. The implants were administered in May and removed in November for a 185 day treatment period. An additional forty calves of similar age and genetic background served as control animals. All calves were weighed at treatment time and again at implant removal. The calves remained with their mothers on grazing lands during the treatment period.

On February 11, all the heifers selected as possible herd replacements were given the standard short-term Syncro Mate-B ™ for estras synchronization (SMB) and artifically inseminated (AI) on February 22. Insemination was performed 48 hours after implant removal without estrus detection. The heifers were AI for an additional 25 day period and followed by clean-up bulls for an additional 30 days. Pregnancy examination was done approximately 90 days after the synchronized breeding to determine date of conception. The heifers were approximately 14–15 months of age at the synchronized breeding. All heifers were palpated per rectum at the SMB treatment time for ovarian structures and cycling activity.

The heifers receiving a long-term implant for 185 days gained 24 lbs. additional body weight compared to controls. This represents an 8.44% increase.

At the time of SMB treatment (11 days prior to AI) 46% of the controls were cycling while 68% of the heifers that had received the long-term implant had shown evidence of reaching puberty.

Conception rate at the synchronized service was 52% for the controls compared to 73% for the heifers that were previously treated. Pregnancy rate at the conclusion of the 25 day AI period was 79% and 89% for each of the respective groups.

EXAMPLE 2

This trial was conducted under the same conditions as Example 1 from May 27 until December 1 with 37 treated heifers and 38 control heifers. Procedures during the long-term implant period were the same as Example 1. These heifers were given the SMB treatment on January 31 and AI on February 10. Subsequent breeding followed the same procedure as outlined in Example 1. The heifers were not palpated at the SMB treatment time. Pregnancy examinations procedures were followed as in Example 1.

The heifers that were used in this study were born approximately 20–30 days after the start of the calving season and therefore were younger than the heifers used in Example 1. The breeding season was also moved 14 days earlier than previous years to avoid calving problems with inclement weather. The age of these heifers at the start of breeding was approximately 12.5 to 13 months.

The average daily gain for the 187 day treatment period was 9.49% greater for the heifer calves subjected to the long-term treatment, a 26 lb. increase in body weight gain.

Conception rate at the synchronized breeding was 41% for the previously treated heifers compared to 27% for the controls. These heifers were not palpated for evidence of cycling activity or puberty prior to the SMB treatment for synchronized breeding, however, their relative young age may explain the lower initial conception rate. Pregnancy at the end of the 25 day AI period was 89% and 77% for the treated control groups.

EXAMPLE 3

Two hundred nine Angus and Simmental heifers were randomly assigned by breed, age and weaning weight to either a long-term treatment group or control on November 7. These heifers were born during February, March and April of the preceding spring. The heifers were weighed and palpated per rectum at implant removal on March 24 and again prior to breeding for evidence of ovarian structure and previous cycling activity. The heifers selected as possible herd replacements were given the SMB treatment on May 1 and AI on May 12 without regard to estrus. Pregnancy diagnosis was made on July 14 and August 24. Implants were the same as used in Examples 1 and 2.

During the long-term treatment period the implanted heifers gained 19 lbs. more than the control heifers. This represents a 10.22% increase.

Pre-synchronization treatment palpation for evidence of cycling activity indicated 60% of the controls and 76% of the treated heifers had cycled at least one time. Conception rate at the synchronized breeding was 21% for the controls and 38% for the long-term treated heifers. Pregnancy rate at the conclusion of the AI period was 52% and 62% for the respective groups.

EXAMPLE 4

Two hundred seventy four Hereford X Simmental heifer calves were randomly assigned to the long-term treatment group and a control group on April 9. The treated calves were implanted with a silastic implant 2.5 cm long×0.35 cm diameter containing 24.00 mg of norgestomet. Implants were removed on October 31. The heifers selected for possible herd replacements were 12–14.5 months old given the standard SMB treatment on February 1 and AI on February 12 of the following year. Twenty five days of additional AI breeding followed by clean-up bulls completed the breeding program. The heifers were pregnancy examined on April 6.

The implant used in this trial was slightly longer than has been previously used in earlier trials resulting in a larger daily elution. With the larger daily elution and insufficient total drug content for the extended treatment period several treated heifers were observed in estrus and became pregnant prior to implant removal.

In this trial the treated heifers gained 7.62% more than the control group during the 205 day period.

Palpation prior to the synchronization treatment showed 74% of the treated group had cycled at least once compared to 53% for the control group. Forty two percent of the long-term group conceived at the synchronized breeding compared to 27% for the control. Twenty five additional days of AI breeding resulted in 83% of the treated group and 67% of the control group diagnosed as pregnant.

SUMMARY

Four trials with over six hundred heifer calves were used to evaluate the growth effect and increased reproductive performance resulting from the long-term administration of norgestomet. Heifer calves that received the long-term implant were 7.3% to 10.2% heavier at the conclusion of the treatment period than the non-treated controls. Heifers that were selected as possible herd replacement and palpated prior to the start of the breeding season showed an increased cycling activity rate of 18% for the treated heifers. Conception rate to a synchronized AI breeding without regard to estrus was 44% for the long-term treated heifers and 28% for the controls. At the end of a 25 day AI period the pregnancy rate for the treated heifers was 78% for the long-term treated heifers compared to 64% for the non-treated heifers. Examples give indications that the long-term implant can increase body weight gain, increase puberty and cycling activity prior to the start of the breeding season and increase conception or pregnancy rate at the start of the breeding season.

What is claimed is:

1. A method for promoting weight gain in a domestic farm animal which comprises subcutaneously implanting a slow-release implant which contains norgestomet in a quantity such that from about 75 to 200 mcg/day is administered for a period of from about 60 to 210 days.

2. A method according to claim 1 wherein the implant is a silastic type implant.

3. A method according to claim 2 wherein the administration period is from 130 to 190 days.

4. A method according to claim 2 wherein the release of norgestomet is 100 to 150 mcg/day.

* * * * *